(12) United States Patent
Farris et al.

(10) Patent No.: US 7,739,128 B2
(45) Date of Patent: Jun. 15, 2010

(54) MEDICAL CLAIMS EVALUATION SYSTEM

(76) Inventors: Alex Farris, 1960 Highway 33, Pelham, AL (US) 35124; Martin C. Nowak, 309 Tutwller Dr., Trussville, AL (US) 35173

( * ) Notice: Subject to any disclaimer, the term of this patent is extended or adjusted under 35 U.S.C. 154(b) by 1060 days.

(21) Appl. No.: 11/160,399

(22) Filed: Jun. 22, 2005

(65) Prior Publication Data

US 2006/0293923 A1    Dec. 28, 2006

(51) Int. Cl.
*G06Q 10/00* (2006.01)
*G06Q 50/00* (2006.01)
(52) U.S. Cl. .......................................... 705/2
(58) Field of Classification Search ............. 705/2, 705/3
See application file for complete search history.

(56) References Cited

U.S. PATENT DOCUMENTS

| 6,223,164 | B1 | 4/2001 | Seare et al. | |
| 6,826,536 | B1 * | 11/2004 | Forman | 705/4 |
| 2004/0078228 | A1 * | 4/2004 | Fitzgerald et al. | 705/2 |
| 2004/0172282 | A1 * | 9/2004 | Benja-Athon | 705/2 |

* cited by examiner

*Primary Examiner*—Gerald J. O'Connor
*Assistant Examiner*—Trang Nguyen
(74) *Attorney, Agent, or Firm*—Smith, Gambrell & Russell

(57) ABSTRACT

A method of determining the efficacy of treatment, correlation of efficacy to specified temporal events, physician and facility efficacy utilizes existing data bases of patient information to determine historic trends relative to patients, physicians, facilities, procedures, date of discharge, length of stay, end of benefits, date of discharge and other variables.

10 Claims, 2 Drawing Sheets

CLAIMS DATA PROJECT

IN-PATIENT FLOW DIAGRAM

MEDICAL CLAIMS EVALUATION SYSTEM

The present invention relates generally to the field of healthcare and more particularly to the areas of practice quality and cost containment. In greater particularity the present invention relates to the reduction in multiple iterations of the same procedures by practitioners with a historic proclivity towards repeat surgeries or other procedures. In even greater particularity the present invention relates to a method for identifying repeat surgeries and their sources and causes. In even greater particularity the present invention relates to the identification of multiple, serial insurance claims, and grouping of claims, to determine patterns of multiple iterations of procedures or surgeries on the same patient, or groups of patients to identify a common practitioner source or common provider facility source. In like manner the present invention relates to the identification of multiple serial insurance claims, and grouping of claims, to determine patterns of health complications following admission, procedures, treatments, interventions, surgeries and the like on the same patient or groups of patients, to identify a common practitioner source or provider facility source of such complications. In even greater particularity the present invention relates to a method for identifying repeat procedures and surgeries or complication and their sources and causes.

Increasing medical costs and insurance costs are one of the leading sources of concern for people of all ages and businesses of all sizes as well as Federal, State and local governments. This includes physicians groups, hospitals, healthcare providers of all types including nursing homes and outpatient facilities, insurers, government agencies, labor groups and investment groups. For the past several decades the rising cost of healthcare and insurance have eaten away at the value of the earnings of all groups. Historically, the trend has been to advise that more research, better facilities, technological advances, and more doctors would solve the dilemma or that public education on medical practices would improve the quality of care patients would expect. All of these things contribute to improving the system, but the rising cost remains unchecked.

This invention addresses one source of medical and insurance costs that can be eliminated or greatly reduced. The savings realized by the implementation of the invention could significantly reduce or even abate the rise in medical and insurance costs. In principal the present invention is based on the understanding that not all patients receive the same quality of care and that not all practitioners have the same level of skill, even though the practitioner and patient have no statistical tools to evaluate the quality of care or the level of skill. Consequently, among patients for whom a lower quality of care is provided greater instances of repeat surgeries are performed, or repeat hospitalizations for the same condition, or repeat treatments or surgeries for the same underlying condition which lead to increased complications impacting the quality of the patients life, increased billing by the physician or subsequent physicians at the same or subsequent facilities and increased cost to the insurers and insured patients.

The present invention contemplates the use of a dynamic database that will provide the statistical and analytical data for use in identifying the sources of sub-quality care or skill whether by a practitioner or a provider facility. The identification of these sources coupled with the subsequent refusal of services to such sources will cause the sources to improve their services or turn to other endeavors, both of which results in improved healthcare and decreased costs.

Accordingly, the present invention contemplates patient specific data from hospital or insurance records that will identify the nature of the patient's illness, the treating physician and facility, the course of treatment, for the illness, and any recurrences of the illnesses. By way of example, patients suffering from a degenerative joint disease may eventually require joint replacement surgery. If a sufficiently large group of patients having such disease can be monitored and historical data maintained with reference to the treating physician and facility, then trends can be documented and physicians or facilities that treat the patients in will have an independent cross referenced record of outcome. More specifically, physicians or facilities that perform abnormally high repeat surgeries or refer excessive numbers of patients to other surgeons for follow up treatment on the previously "repaired" joint can be identified. In a further modification of the invention, statistical analysis can be performed relative to temporal variations in care by observing and quantifying factors such as the time of day or day of week of events such as transfers from ward to ward or facility to facility.

In a still further variation of the invention biographical and institutional data on facilities can be quantified to determine whether background factors in competency and care can be identified. Each of these quantifications makes it possible for the health care user or insurer to screen physicians and facilities to determine whether the patient should submit to treatment or seek treatment elsewhere. The concept is not to obtain a second opinion regarding the patient, but rather an accurate measure on the level of care to be expected by the patient.

These and other objects and advantages of the invention will become apparent from the following detailed description of the preferred embodiment of the invention.

A flow chart for the method of the present invention is depicted in the accompanying drawings which form a portion of this disclosure and wherein.

Figure 1:
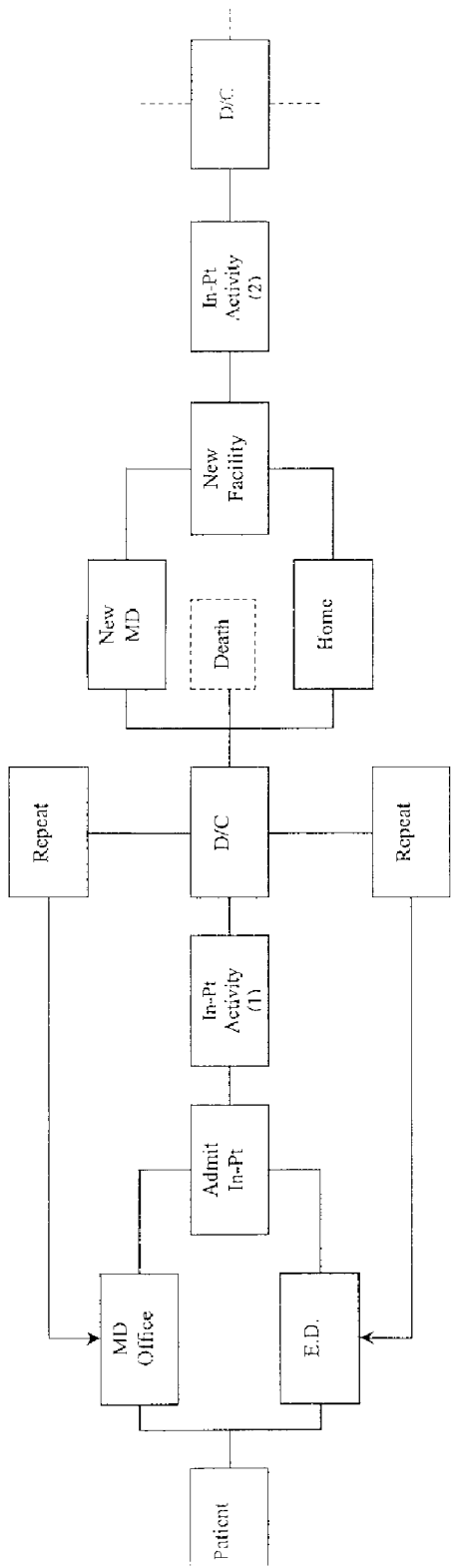
FIG. 1 is an in patient flow diagram of events which may be tracked by the system.
Figure 2:
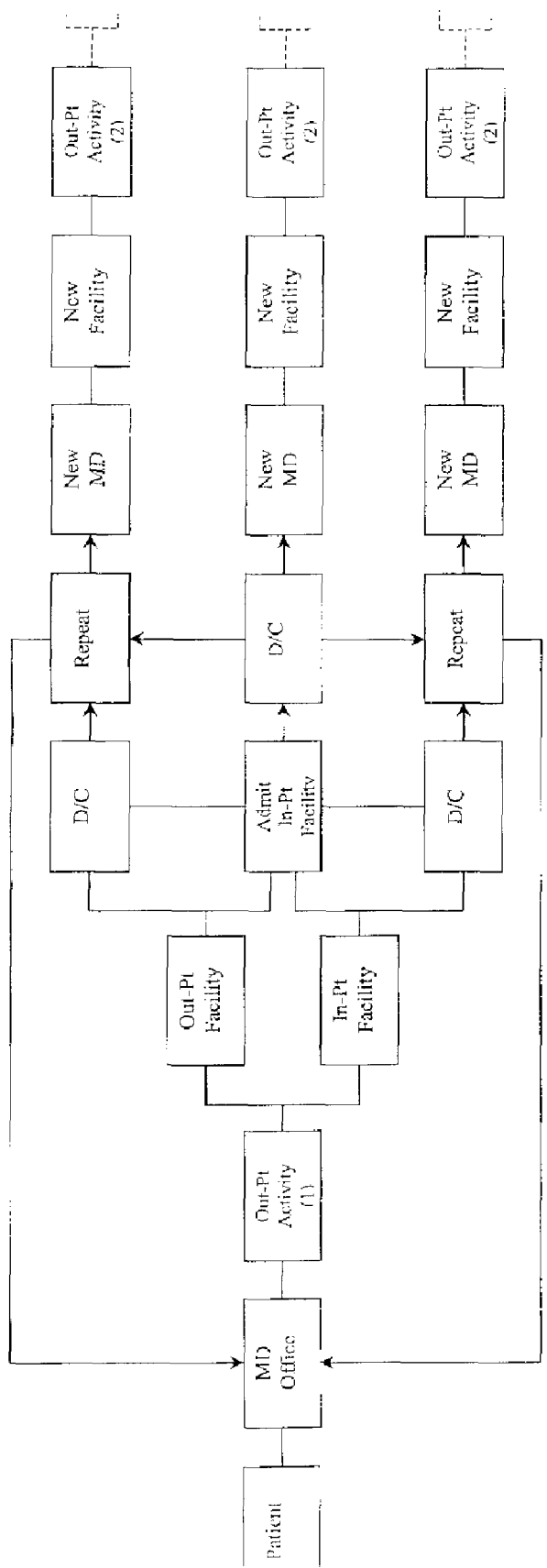
FIG. 2 is an out patient flow diagram of events which may be tracked by the system.

As illustrated in the accompanying figures, the present invention utilizes a database P maintained in a memory of a computer in which discrete pieces of data are collected. Each patient presenting to a practitioner for treatment provides by necessity information regarding the persons identify, age, race, and medical conditions. This information is usually transmitted by the practitioner to an insurer or a government guarantor for payment. In so doing, the practitioner also provides identifying information about itself as well as the diagnosis and treatment provided to the patient on a specific date. All of this data is available in electronic or near electronic form as it is processed by the insurers or guarantors. Each patient can be universally identified by a code such as the patient's social security number. Each healthcare provider can be likewise identified by SSN or taxpayer id or some other unique reference.

Database P includes a permanent file identified with each patient including patient identification and the nature of each occurrence of illness or injury for which the patient has been treated. The information can be transmitted to the database via an interconnected computer network such as the Internet so that data on the same patient may be sent from anywhere the network reaches. For each injury or illness transmitted to the database, data on the date, treatment and identity of the healthcare provider or facility will also be included. Accordingly, the minimum data fields required for the system to work include:

Patient id such as social security number
Facility ID such as Employer tax id number
Procedure ID such as AMA procedure identifier Date and time of each consultation, admission, referral, transfer, or procedure.

Cost of each procedure

Paying party Id such as insurance contract number

Patient data files would include fields for each of the above such that each time patient 121-21-2121 is seen by a physician AL12345 at hospital EI 55-55555 and treated for procedure 033333, a record of the date 01012003 and the cost $500 is created showing that payor BC98765-4 paid for the procedure. Each time procedure 033333 is performed on patient 121-21-2121 another record is created in the patient data file with all of the above information. Accordingly a search query of the database can reveal matches for all patients having repeats of the same procedure. Further refinement of the search allows for determination of patients having repeat procedures wherein the procedure was originally performed by the same physician or at the same facility. Each physician in the database can then be searched to determine such things as percentage of repeat procedures on patients or percentage of referrals to other physicians for repeat procedure or remediation of procedures that proved ineffective.

Using the database in this way, a non-biased profile can be created for any physician, facility, or patient. For each physician who performs like procedures, for example arthroscopy, a peer group analysis can be performed, such that each physician can be evaluated as to his standing within the peer group in terms of percentage of repeat procedures or referrals for repeat procedures. By including biographical data on physicians such as medical school, residencies, training rotations, the analysis also provides for analysis of facility effectiveness in training. It should be further understood that the term database includes distributed file sharing networks, wherein access to various files or databases located on various computers is permitted such that the specific information desired for a particular quantification can be extracted from information on each computer with out transfer of the entire file, such that only the data necessary is copied to the "database" for use in the quantification process.

The data gathering and sampling aspect of the invention is the precursor to the effective utilization of the invention to reduce costs. Each payor enrolled in the program requires each physician or facility that receives reimbursement from the payor to enroll in the system. Each payor then receives periodic reports identifying each physician or facility whose performance as measured by repeat procedures or referrals for repeat procedures is significantly out of the acceptable range as measured against all other physicians who are expected to have the same skill set. That is to say, internists are measured with internist, podiatrist with podiatrists, cardiovascular surgeons with cardiovascular surgeons, psychiatrist with psychiatrist and so on. The payor then has data with which to evaluate the physicians and make recommendations, such as that physician AL12345 should refrain from performing initial procedures of a certain type or that such procedures should not be performed at facility E198765-4. Physician AL12345 may thus continue to diagnose and attend to the care of his patients, however, procedures which his performance leads to an inordinate number or repeats would no longer be reimbursable to him by the payor who would advise the facilities utilized by the patients of this fact. For outpatient procedures, the invention requires pre-approval of all procedures by the payor, thus physicians with diagnostic only payment authorization could not receive approval from their payor Additional factors may also be introduced and tracked with the system including such variables as Length of Stay prior to first discharge for a recurrent treatment, Length of Stay prior to first tracked event; Length of Stay after first tracked event; Length of Stay in subsequent facility; Length of Stay prior to next traced event; Length of Stay after next tracked event. Likewise additional measures can be determined such as mortality rates by physician, facility, activity, or iteration of treatment; physician demographics such as medical school, residency, mentors, year group , experience; or facility demographics such as awards, staffing, licensure, income; and other variables as deemed appropriate.

It is to be understood that the form of the invention shown is a preferred embodiment thereof and that various changes and modifications may be made therein without departing from the spirit of the invention or scope as defined in the following claims.

What is claimed is:

1. A computer based method for measuring iterative medical procedures by by medical providers to determine quality of care based on quantifiable factors comprising the steps of:
   a. creating a procedures database of identified medical procedures in an accessible system memory on a computer system;
   b. creating a provider database by associating individual medical providers with a unique identifier in said provider database on said computer system;
   c. creating a patient database by associating individual patients with a unique identifier in said patient database on said computer system;
   d. electronically deriving anecdotal data for storage in said patient database from sequential medical payment claims provided to said computer system by one or more payers relating to an individual patient within a given time frame, including identification of the medical procedure, identification of the medical provider, and identification of the date of the procedure;
   e. creating a provider history file for each medical provider from said anecdotal data on said computer system;
   f. creating a patient history file for each individual patient from said anecdotal data on said computer system;
   g. iteratively executing a software program referencing each patient history file containing a repetitive medical procedure with each medical provider, wherein a repetitive medical procedure is an identified procedure performed on the same patient by a second medical provider on a date after the date said identified procedure was initially performed by said each medical provider;
   h. determining the percentage of repetitive medical procedures associated with each medical provider as a percentage of all anecdotal data of the same procedure associated with the provider;
   i. determining the standing of each medical provider against like medical providers by said percentage of repetitive medical procedures to indicate quality of care by said medical provider; and
   j. providing a human readable output of the standing of each medical provider to said payer.

2. The method as in claim 1 wherein said deriving step includes identifying the cost associated with each repetitive medical procedure.

3. The method as in claim 1 further comprising iteratively executing a software program referencing each patient history file containing instances of subsequent complications following initial treatment by a provider and correlating identified subsequent common complications with medical providers providing initial treatment to the patient;

determining the percentage of identified subsequent common complications for an identical procedure associated with each medical provider as a percentage of all anecdotal data of the same procedure associated with the provider;

ranking each medical provider against like medical providers by said percentage of identified subsequent common complications for an identical procedure to indicate quality of care by said medical provider; and, Providing each of said rankings of providers to payer institutions in human readable format.

4. A method for electronically measuring medical procedures by source to determine quality of care based on quantifiable factors comprising the steps of:
   a. creating a procedures database of identified medical procedures in an accessible system memory on a computer system;
   b. creating a provider database by associating individual medical providers with a unique identifier in said provider database on said computer system;
   c. creating a patient database by associating individual patients with a unique identifier in said patient database on said computer system;
   d. deriving anecdotal data for storage in said patient database from sequential medical payment claims input to said computer system relating to an individual patient within a given time frame, including identification of the medical procedure, identification of the medical provider, and identification of the date of the procedure;
   e. creating a provider history file for each medical provider from said anecdotal data on said computer system;
   f. creating a patient history file for each individual patient from said anecdotal data on said computer system;
   g. iteratively executing a software program referencing each patient history file containing subsequent treatment by a second provider for an identical procedure on an individual patient is identified and correlating identified subsequent treatments with medical providers providing initial treatment to the patient;
   h. determining the percentage of subsequent treatments by a second provider for an identical procedure associated with each medical provider as a percentage of all anecdotal data of the same procedure associated with the provider; and,
   i. determining the standing of each medical provider against like medical providers by said percentage of subsequent treatment by a second provider for an identical procedure to indicate quality of care by said medical provider; and
   j. providing a human readable output of said standing to a payer.

5. A computer based method for measuring medical procedures by source to determine quality of care based on quantifiable factors comprising the steps of:
   a. creating a procedures database of identified medical procedures in an accessible system memory on a computer system;
   b. creating a provider database by associating individual medical providers with a unique identifier in said provider database on said computer system;
   c. creating a patient database by associating individual patients with a unique identifier in said patient database on said computer system;
   d. electronically deriving anecdotal data for storage in said patient database from sequential medical payment claims submitted to one or more payers relating to an individual patient within a given time frame, including identification of the medical procedure, identification of the medical provider, and identification of the procedure;
   e. creating a provider history file for each medical provider including relevant information from said anecdotal data on said computer system;
   f. creating a patient history file for each individual patient including relevant information from said anecdotal data on said computer system;
   g. iteratively executing a software program to identify each patient history file containing instances of subsequent complications following initial treatment by a provider and correlating identified subsequent common complications with medical providers providing initial treatment to the patient;
   h. determining the percentage of identified subsequent common complications for an identical procedure associated with each medical provider as a percentage of all anecdotal data of the same procedure associated with the provider;
   i. determining the standing of each medical provider against like medical providers by said percentage of identified subsequent common complications for an identical procedure to indicate quality of care by said medical provider; and,
   j. Providing each of said rankings of providers to payer institutions.

6. A method for measuring iterative medical procedures by provider comprising the steps of:
   a. creating a procedures database of identified medical procedures in an accessible system memory on a programmable general purpose computer
   b. creating a provider database by associating individual medical providers with a unique identifier in said provider database in an accessible system memory on said programmable general purpose computer;
   c. creating a patient database by associating individual patients with a unique identifier in said patient database in an accessible system memory on said programmable general purpose compute;
   d. deriving anecdotal data for storage in said patient database from sequential medical payment claims made to a payer relating to an individual patient within a given time frame, including identification of the medical procedure from the procedures identified in said medical procedures database, identification of the medical provider from the providers identified in said provider database, and date of the procedure identified from the medical payment claims;
   e. creating a provider history file for each medical provider from said anecdotal data on said computer system;
   f. creating a patient history file for each individual patient from said anecdotal data on said computer system;
   g. iteratively executing a software program referencing each patient history file containing a subsequent medical procedures associated with common complications from an initial medical procedure with each medical provider;
   h. said software program determining the percentage of subsequent medical procedures associated with common complications from an initial medical procedure associated with each medical provider as a percentage of all anecdotal data of the same initial procedure associated with the medical provider;

i. said computer system ranking each medical provider by said percentage of subsequent medical procedures associated with common complications from an initial medical procedure; and, j. providing a human readable output for each medical provider to said payer for said medical procedures whereby payer's can determine whether to retain such providers services for specific procedures within a payer provider network.

7. A method for using a computer system to create a profile for medical providers, comprising:

a. providing an executable software program in a programmable computer for analyzing information submitted in medical claims presented to a payer;

b. receiving said medical claims in said computer system on an ongoing basis, b. creating a procedures database of identified medical procedures in system memory accessible by said programmable computer;

c. populating a provider database by associating individual medical providers referenced in said medical claims with a unique identifier in said provider database in a system memory accessible by said programmable computer said provider database including a provider history file for each medical provider in said database;

d. populating a patient database by associating individual patients referenced in said medical claims with a unique identifier in said patient database in a system memory accessible by said programmable computer said patient database including a patient history file for each patient in said patient database;

e. deriving anecdotal data for storage in a patient history file in said patient database from sequentially received medical claims for identifiable procedures performed on each patient in said patient database, including identification of the medical procedure from the procedures identified in said medical procedures database, identification of the medical provider performing the procedure, and date of the procedures identified from the medical payment claims;

f. iteratively executing said software program accessing each patient history file containing a repetitive medical procedure wherein a repetitive medical procedure is defined as an identified procedure performed on the same patient by a second medical provider or a first medical provider on a date after the date said identified procedure was initially performed by said first medical provider to store in the provider history file of the first medical provider data reflecting said repetitive medical procedure;

h. executing said software program to determine the standing of said medical provider in terms of percentage of repetitive medical procedures associated with each medical provider; and i. providing a human readable output for each medical provider to said payer.

8. The method as in claim 7 wherein subsequent treatment associated with common complications from an initial medical procedure by a second provider on an patient is identified as a repetitive medical procedure.

9. The method of claim 8 further comprising providing secondary data in said provider history files for each physician identified as a medical provider in said provider database, said secondary data comprising one or more of the following: schools attended, facilities employed by, training rotations, residencies, mentors, year group, experience; iteratively executing said software program accessing said provider history files to correlate common factors among physicians of comparable standing in terms of repetitive medical procedures; and providing a human readable output of said common factors.

10. The method of claim 8 further comprising iteratively executing said software program accessing said patient history files to determine the standing of said first or second medical provider in terms of referrals for repetitive medical procedures.

* * * * *